(12) United States Patent
Reinstein

(10) Patent No.: US 6,614,036 B1
(45) Date of Patent: Sep. 2, 2003

(54) QUALITY ASSURANCE DEVICE FOR A MEDICAL LINEAR ACCELERATOR

(75) Inventor: Lawrence E. Reinstein, Port Jefferson, NY (US)

(73) Assignee: The Research Foundation of the State University of New York, Stony Brook, NY (US)

( * ) Notice: Subject to any disclaimer, the term of this patent is extended or adjusted under 35 U.S.C. 154(b) by 238 days.

(21) Appl. No.: 09/715,517

(22) Filed: Nov. 17, 2000

(51) Int. Cl.[7] .............................. A61N 5/00; G21G 5/00
(52) U.S. Cl. .................................................. 250/492.3
(58) Field of Search ........................... 250/492.1, 492.3

(56) References Cited

U.S. PATENT DOCUMENTS

| | | | | |
|---|---|---|---|---|
| 4,726,046 A | * | 2/1988 | Nunan ..................... | 250/492.1 |
| 5,142,559 A | * | 8/1992 | Wielopolski et al. .... | 250/492.3 |
| 5,553,112 A | * | 9/1996 | Hardy et al. ............. | 378/206 |

OTHER PUBLICATIONS

Mini–Gard™, by Nuclear Associates, Carle Place, New York, 2 pages (no date provided).

* cited by examiner

*Primary Examiner*—John R. Lee
*Assistant Examiner*—James Leybourne
(74) *Attorney, Agent, or Firm*—Dilworth & Barrese

(57) ABSTRACT

A quality assurance device is provided for ensuring the accuracy and reproducibility of the mechanical parameters of medical linear accelerators (Medical LINACs). The quality assurance devices is configured for placement within two parallel slots on the gantry of a Medical LINAC and includes off-the-shelf components for ensuring the accuracy and reproducibility of an optical distance indicator (ODI) distance measurement readout, collimator and gantry angles indicated by a display of the Medical LINAC, a radiation field size indicated by the Medical LINAC display, the centering of cross-hairs on the gantry with the intersection of the Medical LINAC axes, and alignment of the two lasers emanating from two positions toward the Medical LINAC with the intersection of the Medical LINAC axes.

8 Claims, 6 Drawing Sheets

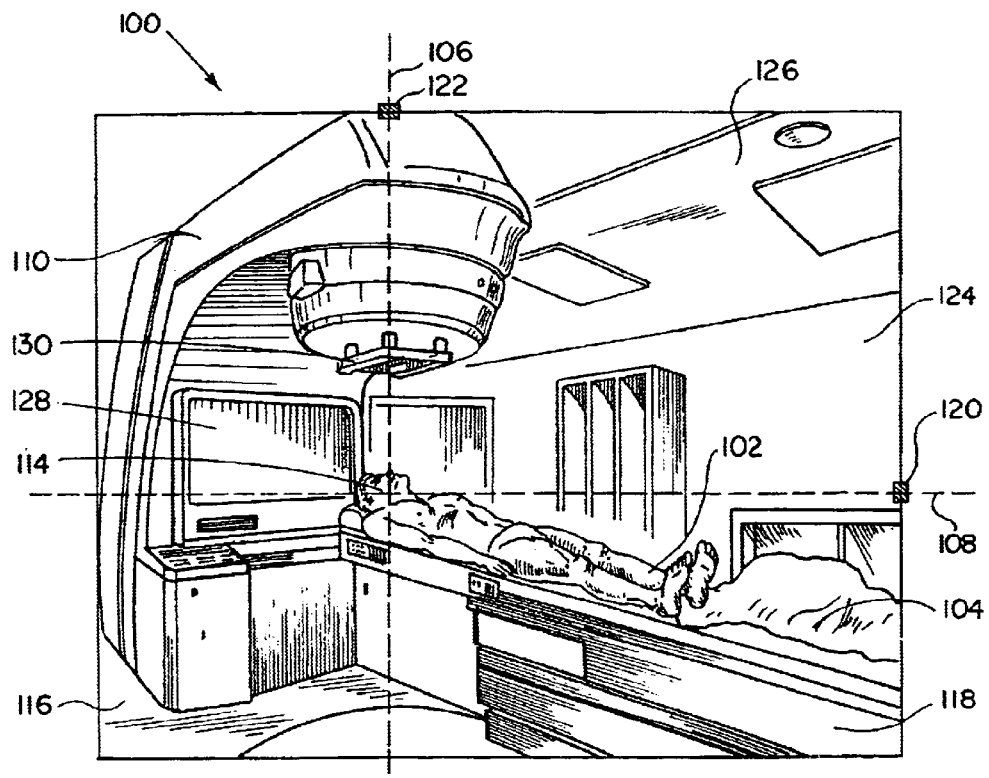
F I G. 1
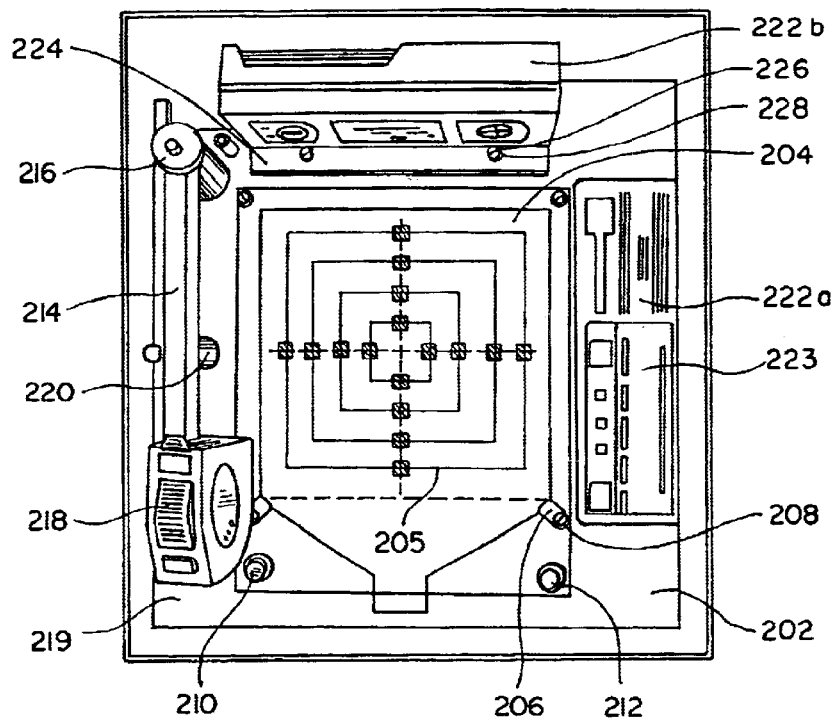
F I G. 2

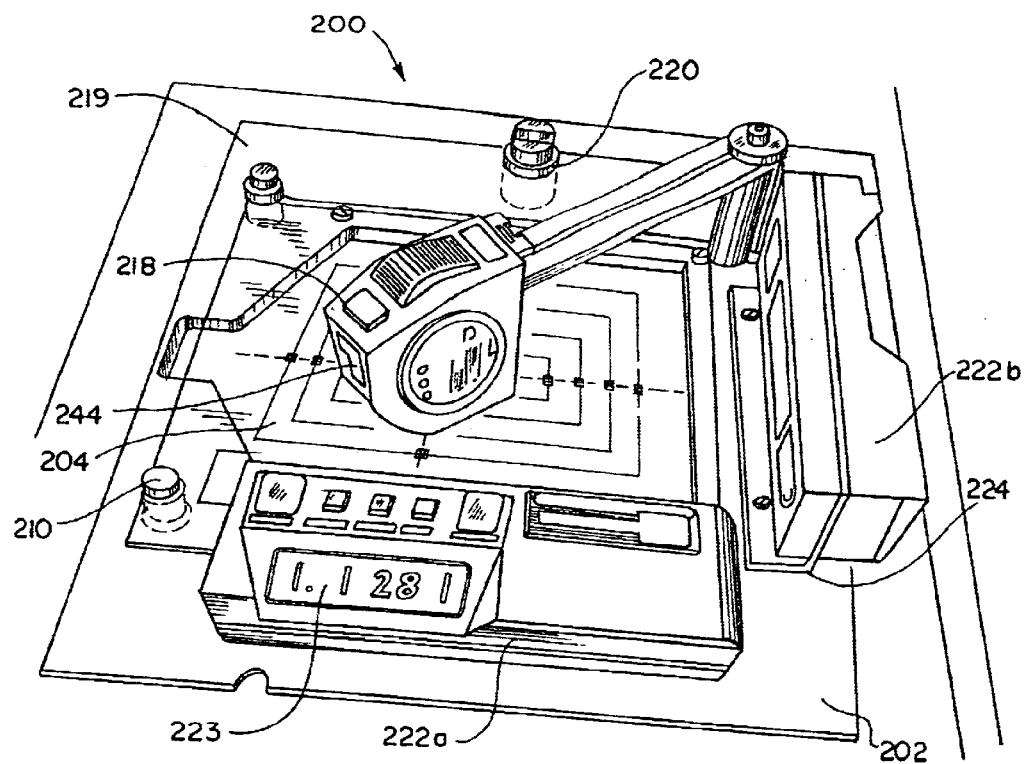
F I G. 3
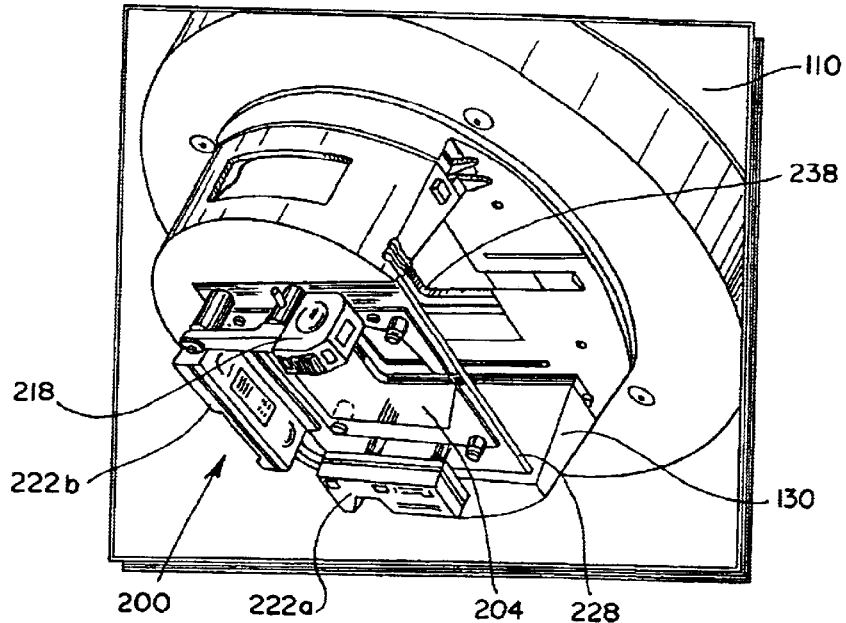
F I G. 4

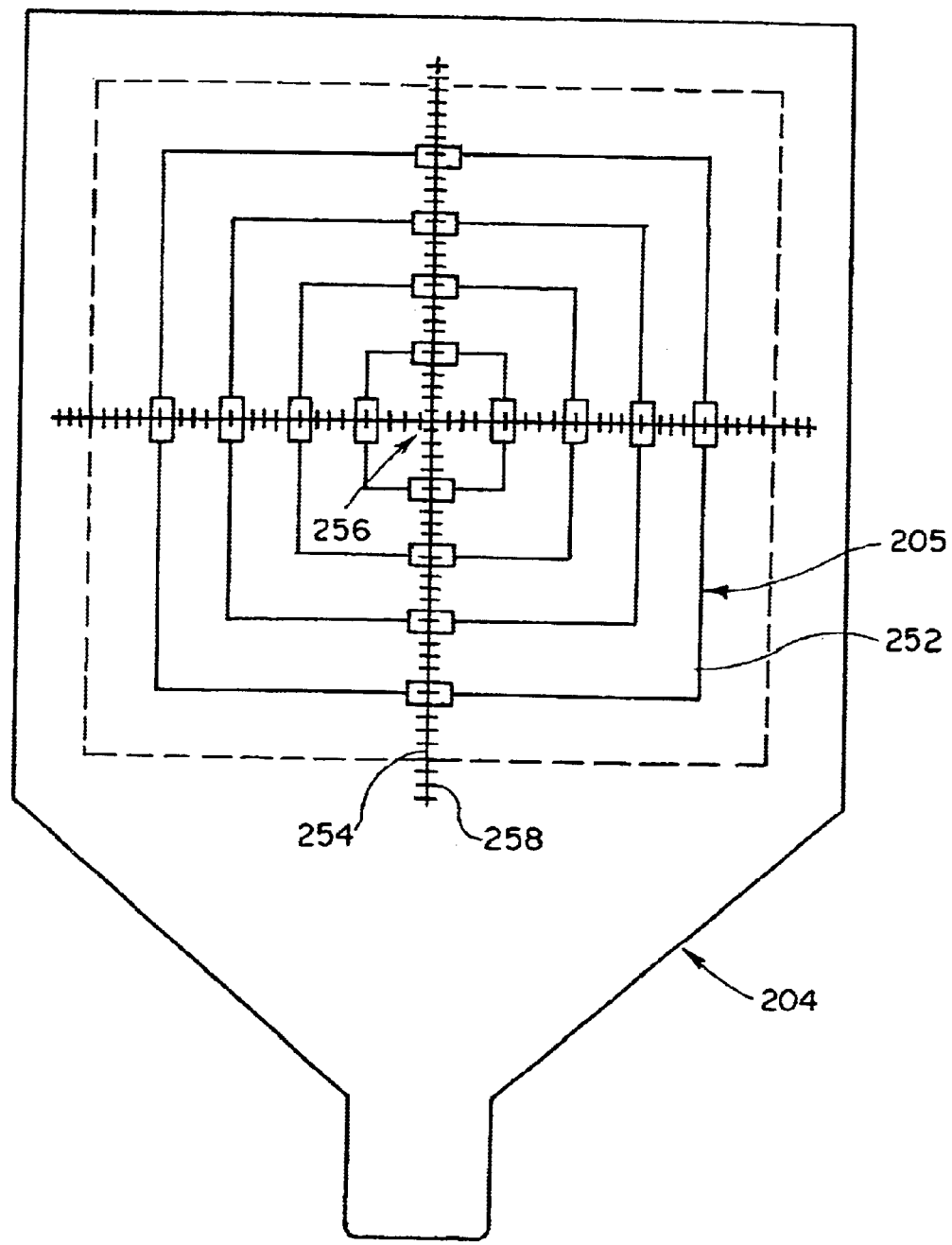
F I G . 8 ly, the present invention relates to a quality assurance device for ensuring the accuracy and reproducibility of the mechanical parameters of a Medical LINAC.

QUALITY ASSURANCE DEVICE FOR A MEDICAL LINEAR ACCELERATOR

BACKGROUND OF THE INVENTION

1. Field of the Invention

The present invention relates to a medical linear accelerator (Medical LINAC). More particularly, the present invention relates to a quality assurance device for ensuring the accuracy and reproducibility of the mechanical parameters of a Medical LINAC.

2. Description of the Related Art

The use of medical linear accelerators (Medical LINACs) for external beam irradiation of patients, principally for the treatment of cancerous tumors, is a well developed field. Medical LINACs have been used for this purpose since the 1940's and are common in most major hospitals around the world. The use of the Medical LINAC for stereotactic external beam irradiation, so-called stereotactic radiosurgery or stereotactic radiotherapy, has been known since around 1984.

FIG. 1 illustrates a prior art Medical LINAC in a general configuration for stereotactic or radiation therapy application designated generally by reference numeral 100. The Medical LINAC 100 is similar to a Medical LINAC of the Varian Clinac Linear Accelerator family manufactured by Varian Medical Systems, Inc., Palo Alto, Calif. The patient's body 102 is on the Medical LINAC platform 104, and a tumor (not shown) is identified within the patient's body 102 and placed at the intersection of the Medical LINAC axes 106, 108; the axis 106 being the vertical axis about which the platform 104 rotates and axis 108 being the horizontal axis about which the gantry 110 of the Medical LINAC 100 rotates.

The Medical LINAC axes 106, 108 are aligned with the tumor by the use of cross-hairs (not shown) on a face plate 112 of the gantry 110 which are projected onto the patient's body 102 to form a cross-hair image 114. The platform 104 is capable of rotating on a bearing within the floor 116, as well as moving up and down on stand 118 and forwards and backwards, in order to position the tumor at the intersection of the cross-hair image 114. Once the center of the cross-hair image 114 is aligned with the tumor, the tumor is most likely at the intersection of the Medical LINAC axes 106, 108.

To ensure that the tumor has been accurately positioned at the intersection of the Medical LINAC axes 106, 108 prior to commencing treatment, three stationary lasers are used. Two lasers (only one laser 120 of the two lasers is shown by FIG. 1) emanate from each side wall 124 and the third laser 122 emanates from a top wall (or ceiling) 126 of the room where the Medical LINAC 100 is located within. If all three lasers are aligned with the tumor, i.e., the lasers intersect the tumor, then the tumor is at the intersection of the Medical LINAC axes 106, 108. If the lasers 120, 122 are not aligned with the tumor, then the tumor is not accurately positioned at the intersection of the Medical LINAC axes 106, 108. Hence, the patient's body 102 is moved by moving the platform 104, in order to place the tumor at the intersection of the Medical LINAC axes 106, 108.

Since the patient's body 102 needs to be moved after aligning the cross-hair image 114 with the tumor, then it may be observed that the cross-hairs are not accurately aligned with the intersection of the Medical LINAC axes 106, 108. However, the case may be that the cross-hairs are accurately aligned with the intersection of the Medical LINAC axes 106, 108, but the lasers 120, 122 are not accurately aligned with the intersection of the Medical LINAC axes 106, 108.

After the laser alignment procedure, the distance of the patient skin surface to the radiation source within the Medical LINAC gantry 110 (i.e., Source-to-Surface Distance (SSD), as known in the art) is ascertained by projecting a scale onto the patient from an oblique angle. The scale is projected using a scale projector mechanically mounted to the Medical LINAC gantry 110 and a scale projector lamp. The distance to the tumor surface is read as the intersection of the scale with the projected cross-hairs. Since the scale projector can loosen and fall out of calibration, it needs to be tested and calibrated periodically. This scale projection of SSD is called an optical distance indicator (ODI).

During treatment of the patient, a beam of radiation emanates from the Medical LINAC 100 towards the tumor. Since the position of the tumor is most likely at the intersection of the two Medical LINAC axes 106, 108, the radiation most likely passes through the tumor.

An adjustable collimator system 130 is attached to the Medical LINAC 100 to collimate the radiation beam into a specific rectangular dimension having a length and width and defining a radiation field size. The collimator system 130 includes mechanical jaws which are typically independent and moveable so as to create the specific rectangular dimension to define the radiation field size. The angle of the collimator system, i.e., the collimator angle, as well as the angle of the Medical LINAC gantry 110, i.e., the gantry angle, are displayed by a digital display 128 of the Medical LINAC 100. These angles are set prior to treatment by moving the gantry 110 and collimator system 130 to positions where the respective angles indicated by the digital display 128 are within a predetermined specification. Once the respective angles are within the predetermined specification, the Medical LINAC gantry 110 and collimator system 130 are stopped from moving. The dimensions of the radiation field size are also displayed by the digital display 128.

As described above, there are many mechanical parameters that are checked and/or set prior to commencing radiation treatment of a patient. For example, the alignment of the cross-hairs with the tumor to ensure that the tumor is at the intersection of the Medical LINAC axes 106, 108 is checked by the use of the two lasers 120, 122, whereas the gantry and collimator angles are set by moving the gantry 110 and collimator system 130 and viewing their respective angles on the Medical LINAC display 128.

Since the mechanical parameters depend on the accurate alignment and placement of various mechanical devices of the Medical LINAC 100, the mechanical parameters tend to shift from their nominal preset values. For example, the alignment accuracy of the cross-hair image 114 depends on the cross-hairs and light source position being accurately aligned with the Medical LINAC axes 106, 108; the radiation field size readout depends on the accurate linkage between a position sensor (e.g., a potentiometer) of the mechanical jaws and the digital display 128; and the ODI distance measurement readout depends on an accurate positioning of the scale projector lamp on the Medical LINAC gantry 110.

Accordingly, like any medical instrument, the Medical LINAC 100 needs to be checked to ensure that a radiation oncology facility can accurately and reproducibly deliver the exact prescribed radiation dose by a medical professional to the tumor. For example, a medical professional needs to check whether the collimator and gantry angles are accurately set at 90.0° and 170.0°, respectively, before setting the collimator and gantry angles to the angles earlier determined for the particular patient. Also, quality control tests need to be performed on the Medical LINAC 100 to ensure the accuracy of the mechanical parameters within predetermined quality control specifications. For example, one needs to ensure that the gantry and collimator angles as indicated by the Medical LINAC display 128 are within ±0.1° and that the centering of the cross-hairs and the alignment of the lasers 120, 122 are within ±0.5 mm.

To achieve these goals, the geometric accuracy of the radiotherapy unit must be tested and verified. It is important to at least test and verify that the following mechanical parameters are within the predetermined specifications: the ODI distance measurement readout, the gantry and collimator angles indicated by the Medical LINAC display 128, the centering of the cross-hairs with the intersection of the Medical LINAC axes 106, 108, the radiation field size indicated by the Medical LINAC display 128, and the alignment of the two lasers 120, 122 with the intersection of the Medical LINAC axes 106, 108.

Accordingly, there exists a need for a quality assurance device for testing and verifying that several mechanical parameters of a Medical LINAC are within predetermined specifications to ensure accuracy and reproducibility of the mechanical parameters.

SUMMARY OF THE INVENTION

The present invention provides a quality assurance device for ensuring the accuracy and reproducibility of several mechanical parameters of a Medical Linear Accelerator (Medical LINAC). The quality assurance device is configured for placement within two parallel slots on the gantry of the medical LINAC and includes off-the-shelf components for ensuring the accuracy and reproducibility of an optical distance indicator (ODI) distance measurement readout, collimator and gantry angles indicated by a display of the Medical LINAC, a radiation field size indicated by the Medical LINAC display, the centering of cross-hairs on the gantry with the intersection of the Medical LINAC axes, and alignment of the two lasers emanating from two positions toward the Medical LINAC with the intersection of the Medical LINAC axes.

BRIEF DESCRIPTION OF THE DRAWINGS

Preferred embodiments of the invention are described below with reference to the drawings, which are described as follows:

FIG. 1 illustrates a prior art medical linear accelerator (Medical LINAC) used for stereotactic radiosurgery;

FIG. 2 is a top view of a quality assurance device for ensuring the accuracy and reproducibility of the mechanical parameters of the Medical LINAC according to the present invention;

FIG. 3 is a perspective view of the quality assurance device of FIG. 2;

FIG. 4 is a perspective view of the quality assurance device of FIG. 2 placed within a slot of a gantry of the Medical LINAC of FIG. 1;

FIG. 8 is a top view of a plexiglass which is mounted onto a base of the quality assurance device of FIG. 2;

DETAILED DESCRIPTION OF THE PREFERRED EMBODIMENTS

Figure 5:
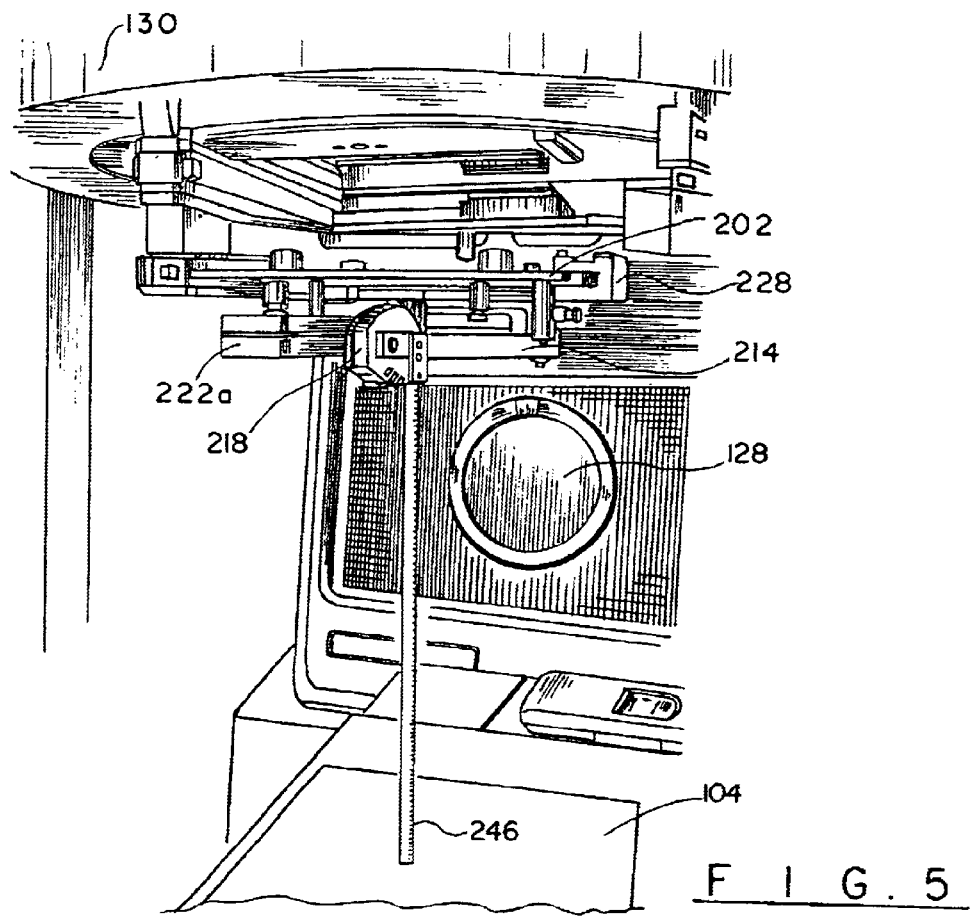
FIG. 5 is a perspective view showing the quality assurance device of FIG. 2 being used to measure a distance from the device to a platform of the Medical LINAC.

The present invention provides a quality assurance device which tests and verifies that the mechanical parameters of a medical linear accelerator (Medical LINAC), as shown by FIG. 1, are within predetermined specifications to ensure accuracy and reproducibility of the mechanical parameters. The quality assurance device can also be used to test and verify the Medical LINAC mechanical parameters for a particular patient prior to commencing treatment to ensure accuracy and reproducibility of the mechanical parameters. The mechanical parameters need to be tested and verified in order that a radiation oncology facility accurately and reproducibly delivers the exact prescribed radiation dose to a tumor within a patient, during radiation therapy.

The quality assurance device of the present invention is configured for placement within two parallel slots on the gantry 110 of the Medical LINAC 100 and includes off-the-shelf components for ensuring the accuracy and reproducibility of an optical distance indicator (ODI) distance measurement readout, collimator and gantry angles indicated by the display 128 of the Medical LINAC 100, a radiation field size indicated by the Medical LINAC display 128, the centering of cross-hairs on the gantry 110 with the intersection of the Medical LINAC axes 106, 108, and alignment of the two lasers 120, 122 emanating from two walls 124, 126 toward the Medical LINAC 100 with the intersection of the Medical LINAC axes 106, 108.

With reference to FIGS. 2 and 3, there are shown top and perspective views of the quality assurance device of the present invention which is capable of ensuring the accuracy and reproducibility of the mechanical parameters of the Medical LINAC 100. The quality assurance device is designated generally by reference numeral 200 and includes a base 202, a plexiglass 204, four spring-loaded screws 206 which align with tapped holes 208 on the base 202 for mounting the plexiglass 204 to the base 202, and two thumb screws 210 which align with tapped holes 212 on the base 202 for locking the plexiglass 204 in position.

The quality assurance device 200 further includes a swing arm mechanism 214 having a swing arm stop 216 attached to a digital tape measure 218 for allowing the digital tape measure 218 to swing to a 45-degree angle with respect to an edge 219 of the base 202 (see FIGS. 3 and 5), a swing arm locking mechanism 220, two digital angulometers 222a, 222b, two mounting plates 224 and two pairs of screws 226 which align with mounting holes 228 on the base 202 for orthogonally mounting the digital angulometers 222a, 222b with respect to each other to the base 202.

The thickness of the base 202 is approximately 0.64 cm and the width and length of the base 202 are approximately 30.00 cm. These dimensions permit the base 202 to be fitted and locked within two parallel slots 228 on the face of the Medical LINAC gantry 110 as shown by FIG. 4.

The swing arm mechanism 214 having the swing arm stop 216 and the swing arm locking mechanism 220 are known in the art and are not described in detail herein. The digital tape measure 218 can be any known digital tape measure known in the art. The digital angulometers 222a, 222b are preferably the SMARTTOOL™ digital angulometers available from Macklanburg-Duncan, Oklahoma City, Okla.

With continued reference to FIGS. 2 and 3, one of the digital angulometers 222a is mounted with the digital readout facing up, while the other digital angulometer 222b is mounted to the base 202 with the digital readout facing away from the device 200. The digital angulometer 222a is used to measure the collimator angle and the other digital angulometer 222b is used to measure the gantry angle as further described below with reference to FIG. 6. The plexiglass 204 includes various markings 205 which are further described below with reference to FIGS. 7–10.

A description will now be given with respect to testing and verifying the mechanical parameters of the Medical LINAC 100 using the quality assurance device 200 of the present invention. The device 200 is used for testing and verifying the following six mechanical parameters of the Medical LINAC 100: the distance from a face plate 112 of the Medical LINAC gantry 110 to a platform 104 of the Medical LINAC 100 (i.e., verifies the ODI distance measurement readout), collimator and gantry angles indicated by a display 128 of the Medical LINAC 100, a radiation field size indicated by the Medical LINAC display 128, the centering of cross-hairs 238 on the gantry 110 with the intersection of the Medical LINAC axes 106, 108, and alignment of the two lasers 120, 122 emanating from two walls (not shown) toward the Medical LINAC 100 with the intersection of the Medical LINAC axes 106, 108.

A. Verifying the ODI Distance Measurement

With reference to FIG. 5, there is shown a perspective view showing the quality assurance device of FIG. 2 being used to measure the distance from the gantry face plate 112 (i.e., the location of the quality assurance device 200) to the Medical LINAC platform 104. The digital tape measure 218 having a digital readout 244 and a tape measure 246 is moved to a 45-degree angle with respect to the edge 219 of the base 202 using the swing arm mechanism 214.

As mentioned above, the swing arm mechanism 214 includes a swing arm stop 216 configured for stopping the digital tape measure 218 when the digital tape measure 218 is at 45-degrees with respect to the edge 219. At this position, the digital tape measure 218 is situated along the central axis of a radiation beam path, i.e., the path of the radiation beam capable of being emanated by the Medical LINAC 100. It is important that the swing arm mechanism 214 stops and aligns the tape measure 246 of the digital tape measure 218 exactly along the central axis of the radiation beam path to measure the SSD accurately and test the ODI.

While the digital tape measure 218 is at 45-degrees with respect to the edge 219, the operator guides the tape measure 246 towards the Medical LINAC platform 104 and reads the distance from the device 200 to the platform 104 from the digital readout 244. It is preferred that the distance measurement is read from the digital readout 244 rather than the tape measure 246, since the digital readout 244 provides a more accurate reading than the tape measure 246.

The distance measurement read from the digital readout 244 is then compared with a distance measurement displayed by the ODI (not shown) on the Medical LINAC display 128. If the ODI distance measurement is significantly different from the distance measurement provided by the digital readout 244 and an offset distance added thereto which takes into account the distance from the base 202 to the radiation source within the Medical LINAC gantry 110, then the Medical LINAC 100 must be calibrated appropriately until the ODI distance measurement is identical to the measurement provided by the digital readout 244 or until the ODI distance measurement is within the predetermined specifications, e.g., within ±1.0 mm.

When the distance measurement process has been completed the digital tape measure 218 is swung back towards the edge 219 of the base 202 and locked into position by the swing arm locking mechanism 220.

B. Verifying the Gantry and Collimator Angles

Figure 6:
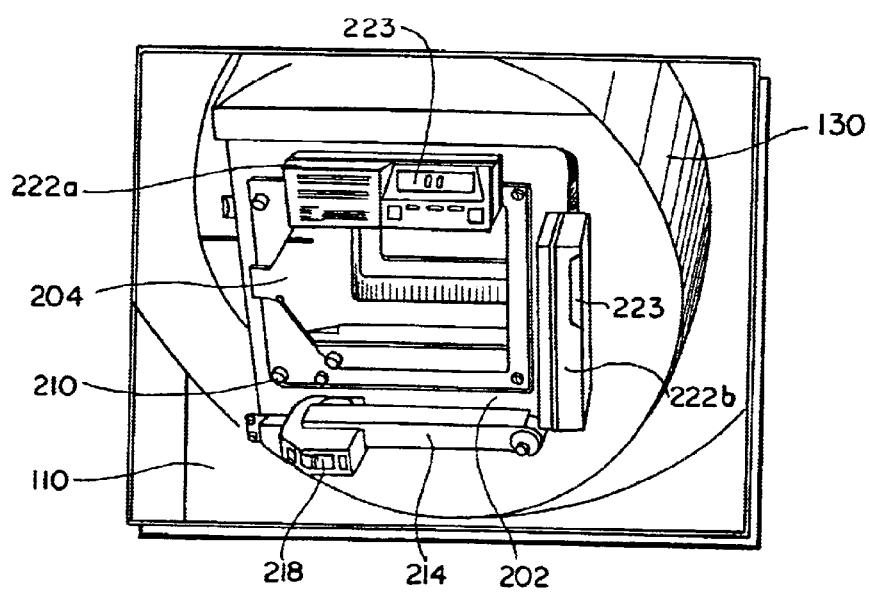
FIG. 6 is a perspective view showing the quality assurance device of FIG. 2 being used to measure collimator and gantry angles.

With reference to FIG. 6, the gantry and collimator angles are tested and verified against angle reading provided by the Medical LINAC display 128 by using the two angulometers 222a, 222b as indicated above. The digital angulometer 222a is used to measure the collimator angle and the other digital angulometer 222b is used to measure the gantry angle.

The gantry angle is measured by rotating the Medical LINAC gantry 110 to an angle of 90° or 270° and reading the angle measurement provided by the digital readout 223 of the digital angulometer 222b as shown by FIG. 6. The angle measurement is then compared with a gantry angle measurement provided by the Medical LINAC display 128.

It is contemplated for the digital angulometer 222b to include audible means for providing an audible sound when the Medical LINAC gantry 110 is rotated by multiples of 90°. For example, an operator can rotate the Medical LINAC gantry 110 to a position where the audible sound is heard and check the digital readout 223 to determine how many degrees the Medical LINAC gantry 110 was rotated, i.e., 0°, 90°, 180°, etc. The operator can then check the Medical LINAC display 128 to determine if it provides a readout identical to the readout provided by the digital readout 223 of the digital angulometer 222b. That is, if the Medical LINAC gantry 110 was rotated to an angle of 90°, does the digital display 128 display a reading of 90°.

If the gantry angle measurement provided by the Medical LINAC display 128 is significantly different from the gantry angle measurement provided by the digital readout 223, then the Medical LINAC 100 must be calibrated appropriately until the gantry angle measurement provided by the Medical LINAC display 128 is identical to the gantry angle measurement provided by the digital readout 223 or until the gantry angle measurement provided by the Medical LINAC display 128 is within the predetermined specifications, e.g., within ±0.1. The digital angulometer 222b can then be turned off by pushing the on/off button 250.

After the gantry angle is measured and with the Medical LINAC gantry 110 pointing horizontally, i.e., the gantry angle is at 90° or 270°, the collimator angle can be measured by reading the angle measurement provided by the digital readout 223 of the digital angulometer 222a as shown by FIG. 6. The angle measurement is then compared with a collimator angle measurement provided by the Medical LINAC display 128.

It is contemplated for the digital angulometer 222a to include audible means for providing an audible sound when the collimator system 130 is at an angle that is a multiple of 90°. Upon hearing the audible sound, the operator can then check the Medical LINAC display 128 to determine if it provides a readout identical to the readout provided by the digital readout 223 of the digital angulometer 222a. That is, if the collimator system 130 is at an angle that is a multiple of 90°, does the digital display 128 display a similar or identical reading.

If the collimator angle measurement provided by the Medical LINAC display 128 is significantly different from the collimator angle measurement provided by the digital readout 223, then the Medical LINAC 100 must be calibrated appropriately until the collimator angle measurement provided by the Medical LINAC display 128 is identical to the collimator angle measurement provided by the digital readout 223 or until the collimator angle measurement provided by the Medical LINAC display 128 is within the predetermined specifications, e.g., within ±0.1. The digital angulometer 222a can then be turned off by pushing an on/off button 250.

C. Verifying the Dimensions of the Radiation Field

Figure 7:
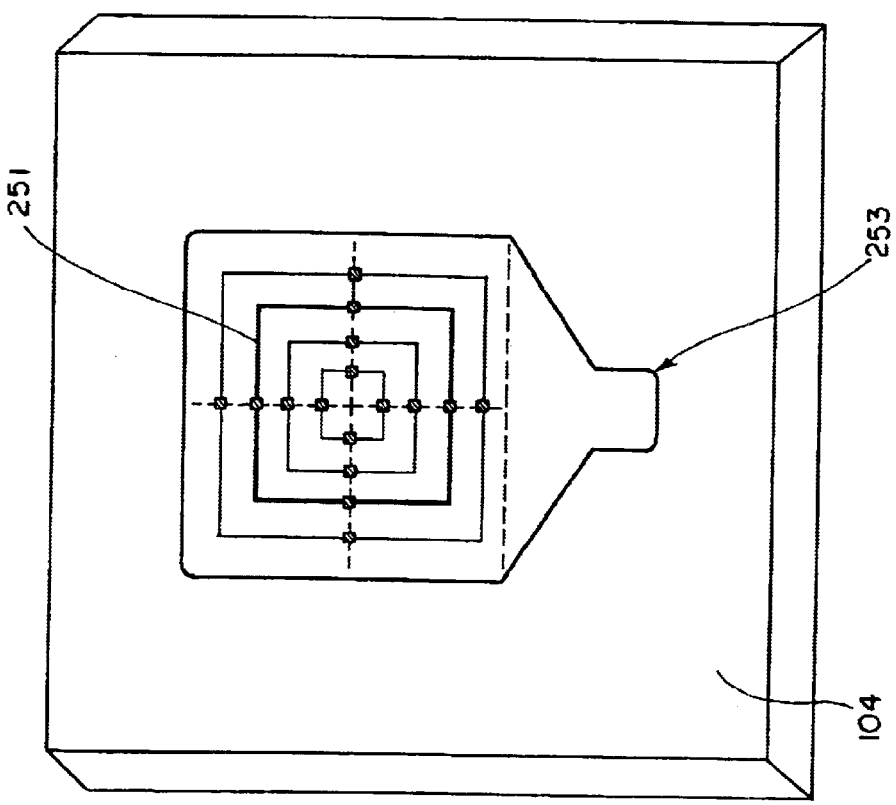
FIG. 7 is a top view of a Medical LINAC platform illustrating the measurement of the dimensions of a radiation field according to the present invention.

With reference to FIGS. 7 and 8, a description will now be provided for measuring and verifying the dimensions of a radiation field against the dimensions displayed by the Medical LINAC display 128 using the quality assurance device 200. The radiation field produced by the Medical LINAC 100 is generally rectangular-shaped and is controlled by the collimator system 130 which is attached to the Medical LINAC gantry 110 to collimate the radiation beam. The collimator system 130 typically includes four rectangular jaw structures which are movable to change the radiation field size of the rectangular-shaped radiation field.

In order to determine the radiation field size, the four rectangular jaw structures or other components of the collimator system 130 are moved and the dimensions of the radiation field size are viewed on the Medical LINAC display 128 as known in the art. The shape of the radiation field can be ascertained by projecting a light localizer field onto the Medical LINAC platform 104 to form a light field image 251 as shown by FIG. 7. The light field image 251 is projected onto the platform 104 by turning on a light source within the Medical LINAC gantry 110 behind the rectangular jaw structures of the collimator system 130. When the quality assurance device 200 is inserted within the two parallel slots 228 of the gantry 110, the light source also projects the markings 205 on the plexiglass 204 to form a projected markings image 253 on the Medical LINAC platform 104.

With reference to FIG. 8, the markings 205 include a series of concentric squares 252 and two intersecting lines 254 forming cross-hairs 256 at the intersection. The two intersecting lines 254 have calibration lines 258. When the markings 205 are projected onto the Medical LINAC platform 104 to form the projected markings image 253, each calibration line 258 is preferably 1.0 mm from an adjacent calibration line 258 when the plexiglass 204 is preferably at a precise distance of 100.0 cm SSD. Also, when the plexiglass 204 is preferably at a precise distance of 100.0 cm SSD, the series of concentric squares 252 and the calibration lines 258 specify various radiation field sizes in centimeters. For example, the innermost or first concentric square indicates a radiation field size of 5.0 cm×5.0 cm, the second concentric square indicates a radiation field size of 10.0 cm×10.0 cm, the third concentric square indicates a radiation field size of 15.0 cm×15.0 cm, and the fourth concentric square indicates a radiation field size of 20.0 cm×20.0 cm. It is contemplated that the markings 205 on the plexiglass 204 may be sized to provide accurate radiation field sizes when the plexiglass 204 is at a distance in the range of 80.0 to 150.0 cm SSD.

In order to verify the dimensions of the radiation field as indicated by the Medical LINAC display 128, the projected concentric squares and calibration lines of the projected markings image 253 are used to measure the dimensions of the light field image 251, and hence the actual dimensions of the radiation field. This is accomplished by the operator noting which projected concentric square the rectangular-shaped light field image 251 overlaps, as shown by FIG. 7. The concentric square overlapped by the light field image 251 provides the length and width of the radiation field or the dimensions of the radiation field. The measured dimensions are then compared with the dimensions provided by the Medical LINAC display 128.

If the dimensions of the radiation field provided by the Medical LINAC display 128 are significantly different from the measured dimensions using the quality assurance device 200, then the system of the Medical LINAC 100 which measures the radiation field must be calibrated appropriately until the dimensions provided by the Medical LINAC display 128 are identical to the measured dimensions or until the dimensions of the radiation field provided by the Medical LINAC display 128 are within the predetermined specifications, e.g., within ±1.0 mm.

D. Verifying Cross-hair Centering

Figure 9:
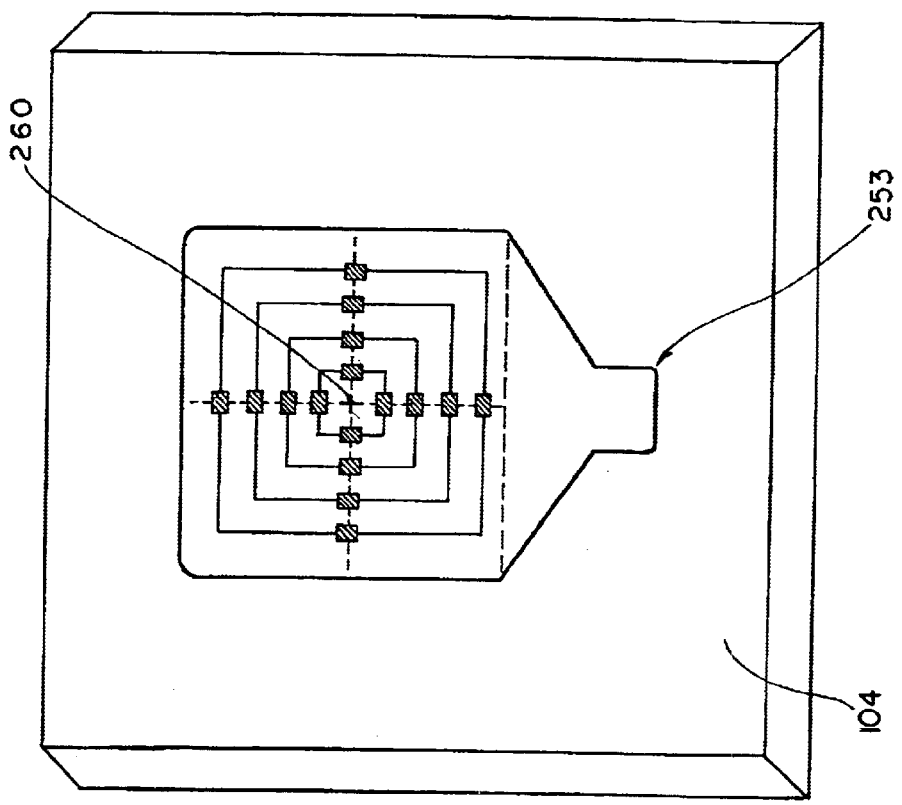
FIG. 9 is a top view of the Medical LINAC platform illustrating verification of the centering of cross-hairs projected from the gantry of the Medical LINAC according to the present invention.

FIG. 9 is a perspective view showing the quality assurance device 200 being used to ascertain whether the center of a cross-hair image 260 projected from the Medical LINAC gantry 110 is positioned at the intersection of the Medical LINAC axes 106, 108. One of the axis of the Medical LINAC axes 106, 108 being the vertical axis about which the platform 104 rotates and the other axis being the horizontal axis about which the gantry 110 rotates.

The cross-hair image 260 is used to position the tumor in the path of the radiation beam which is along the intersection of the Medical LINAC axes 106, 108. Specifically, the intersection of the two Medical LINAC axes 106, 108 is the point where all of the radiation converges for any position of the platform 104 or gantry 110. If the center of the cross-hair image 260 does not coincide with the intersection of the Medical LINAC axes 106, 108, then the tumor would not be accurately positioned in the path of the radiation beam.

In order to verify whether the center of the cross-hair image 260 is at the intersection of the Medical LINAC axes 106, 108, the light source is once again used, as described above with reference to FIG. 7, to project the markings 205 on the plexiglass 204 onto the platform 104 to form the projected markings image 253. The center of the two intersecting lines 254 is preset to define the center of the intersection of the Medical LINAC axes 106, 108.

If the center of the cross-hair image 260 does not overlap with the center of the two intersecting lines of the projected markings image 253, then the center of the cross-hair image 260 also does not overlap with the intersection of the Medical LINAC axes 106, 108. If this cross-hair image 260 is not corrected to overlap with the intersection of the Medical LINAC axes 106, 108, a medical professional is apt to position the tumor at a position which is not in the path of the radiation beam.

To prevent this from occurring the Medical LINAC 100 must be calibrated in order for the cross-hair image 260 to overlap with the center of the two intersecting lines of the markings image 253. Once the center of the cross-hair image 260 overlaps with the center of the two intersecting lines of the markings image 253, the center of the cross-hair image 260 also overlaps with the intersection of the Medical LINAC axes 106, 108, and the tumor can be accurately positioned.

It is preferred to verify that the cross-hair image 260 is centered at the intersection of the Medical LINAC axes 106, 108 within ±0.5 mm.

E. Verifying Alignment of Lasers

Figure 10A:
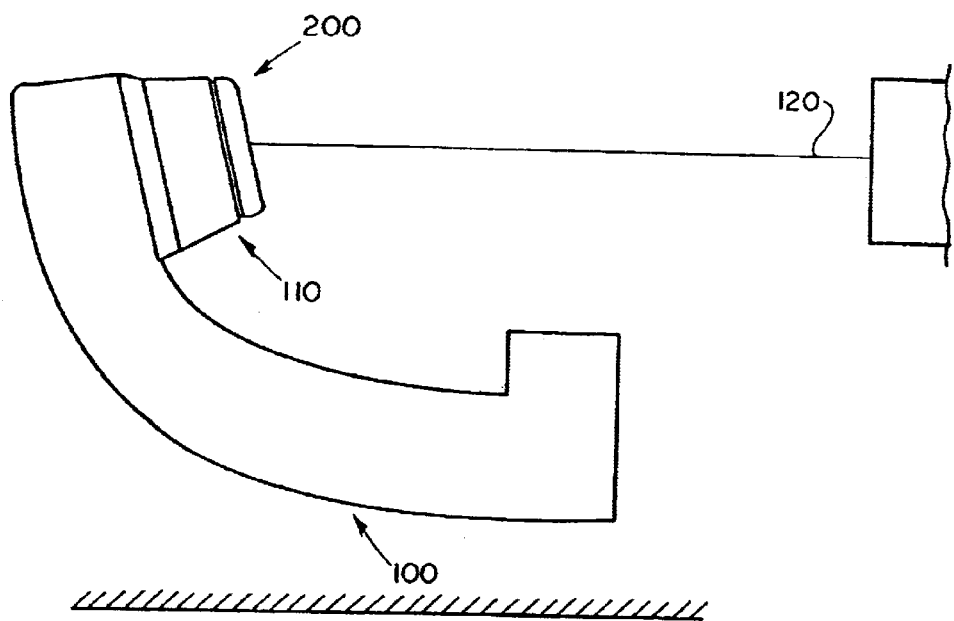
FIG. 10A is a perspective view of the Medical LINAC gantry illustrating alignment verification of a laser emanating toward the Medical LINAC from a side position according to the present invention.
Figure 10B:
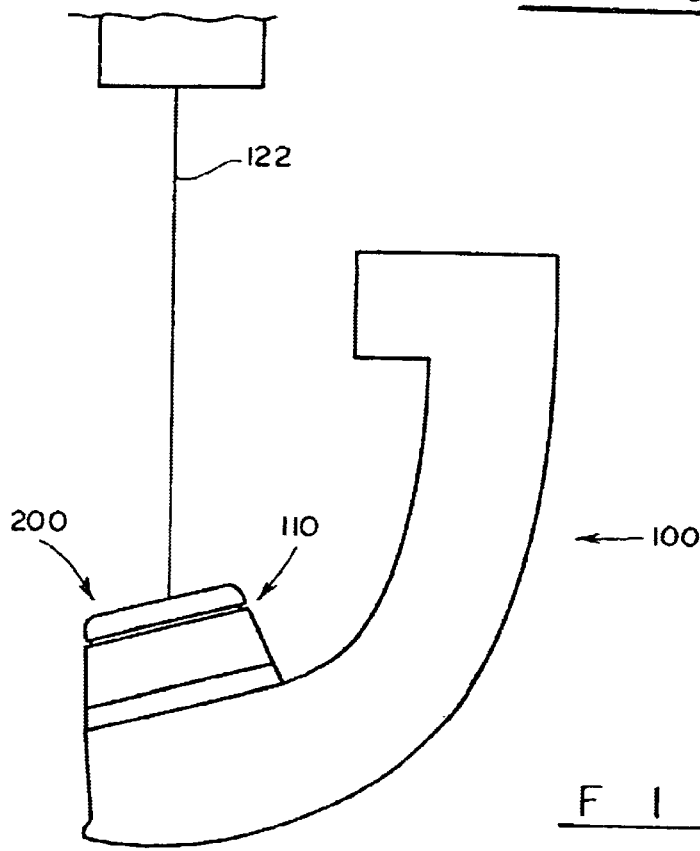
FIG. 10B is a perspective view of the Medical LINAC gantry illustrating alignment verification of a laser emanating toward the Medical LINAC from a top position according to the present invention.

With reference to FIGS. 10A and 10B, there are shown perspective views of the quality assurance device 200 being used to verify the alignment of the three lasers (only two of the three lasers, namely, lasers 120, 122, are shown by FIGS. 10A and 10B, respectively); each one of the three lasers emanates toward the Medical LINAC 100. The three lasers are used as a backup to check whether the tumor is positioned at the intersection of the Medical LINAC axes 106, 108.

Two side wall lasers (only one side wall laser, namely, laser 120, is shown by FIG. 10A) are directed toward the Medical LINAC 100 from positions on the side walls (left and right walls) of the room having the Medical LINAC 100 and the other laser 122 is directed toward the Medical LINAC 100 from a position on top of the Medical LINAC 100. The side positions and the top position are substantially orthogonal with respect to each other and are selected in order for the lasers 120, 122 to intersect at a point which coincides with the intersection of the Medical LINAC axes 106, 108.

The two lasers emanating from the side walls are positioned to be situated along the horizontal axis of the Medical LINAC gantry 110 when the Medical LINAC gantry 110 is at the upright or rest position and the third laser 122 is positioned to be situated along the vertical axis of the Medical LINAC platform 104 when the Medical LINAC platform 104 is at the home position, i.e., directly below the Medical LINAC gantry 110 when the Medical LINAC gantry 110 is at the upright position.

To ascertain whether the lasers 120, 122 intersect at the Medical LINAC axes 106, 108, one must ascertain whether the side lasers are projected or aligned along the horizontal axis of the Medical LINAC 100 and whether the top laser 122 is projected or aligned along the vertical axis of the Medical LINAC 100. Accordingly, first, the Medical LINAC gantry 110 is rotated 90°, as shown by FIG. 10A, to determine whether the side laser 120 coincides with the center of the cross-hairs 256 on the plexiglass 204. It is also noted that the Medical LINAC gantry 110 can be rotated 270° and the laser emanating from the side wall opposite the side wall from where the laser 120 is emanating from can be used to determine whether that laser coincides with the center of the cross-hairs 256 on the plexiglass 204. If the side laser used during the alignment test coincides with the center of the cross-hairs 256, then the side laser is aligned with horizontal axis of the Medical LINAC 100. If not, then the side laser must be calibrated in order for the side laser to coincide with the center of the cross-hairs 256. Once the side laser coincides with the center of the cross-hairs 256, the side laser is aligned with the horizontal axis of the Medical LINAC 100.

Second, the Medical LINAC gantry 110 is rotated 180°, as shown by FIG. 10B, to determine whether the laser 122 coincides with the center of the cross-hairs 256 on the plexiglass 204. If the laser 122 coincides with the center of the cross-hairs 256, then the laser 122 is aligned with vertical axis of the Medical LINAC 100. If not, then the laser 122 must be calibrated in order for the laser 122 to coincide with the center of the cross-hairs 256. Once the laser 122 coincides with the center of the cross-hairs 256, the laser 122 is aligned with the vertical axis of the Medical LINAC 100.

It is preferred to verify that the lasers 120, 122 are aligned with the intersection of the Medical LINAC axes 106, 108 within ±0.5 mm.

F. Additional Considerations

It is contemplated that the quality assurance device of the present invention can also be used to measure the distance of the radiation source to the patient for setup, prior to commencing radiation treatment.

Further, it is contemplated to use the quality assurance device of the present invention to measure extended distances to the patient. That is, distances which are greater than 120 cm and are thereby beyond the range of the ODI.

It will be understood that various modifications can be made to the various embodiments of the present invention herein disclosed without departing from its spirit and scope. Therefore, the above description should not be construed as limiting the invention but merely as presenting preferred embodiments of the invention. Those skilled in the art will envision other modifications within the scope and spirit of the present invention as defined by the claims presented below.

What is claimed is:

1. A device for measuring at least one parameter of a medical linear accelerator (Medical LINAC), said device comprising:
    a base defining a border around an central region;
    at least one angulometer positioned on the base;
    at least one tape measure mounted to the base; and
    a transparent fixture mounted on the base and including markings thereon, wherein the markings are substantially overlaid over the central region of the base.

2. The device according to claim 1, wherein the border is dimensioned for being inserted within a slot on a gantry of the Medical LINAC.

3. The device according to claim 1, wherein the assembly includes a swing arm connected to the at least one tape measure capable of swinging the at least one tape measure at a position substantially above the central region of the base.

4. The device according to claim 3, wherein the swing arm is configured for swinging the at least one tape measure at a 45-degree angle with respect to an edge of the base and aligning the at least one tape measure with a central axis of a radiation beam path defined by the Medical LINAC.

5. The device according to claim 3, further comprising a locking mechanism for locking the swing arm.

6. The device according to claim 1, wherein the markings define various radiation field sizes of a radiation field produced by the Medical LINAC when the markings are projected at a Source-to-Surface Distance (SSD) of approximately 80 to 150 cm.

7. The device according to claim 1, wherein the markings define the vertical and horizontal axes of the Medical LINAC.

8. The device according to claim 1, wherein the at least one parameter is selected from the group consisting of, distance from a point on the gantry of the Medical LINAC to a platform of the Medical LINAC; collimator angle of a collimator of the Medical LINAC; gantry angle of the gantry of the Medical LINAC; radiation field size of a radiation field produced by the Medical LINAC; centering of crosshairs projected from the gantry of the Medical LINAC with the intersection of the Medical LINAC axes; and alignment of two lasers emanating from two positions toward the Medical LINAC with the intersection of the Medical LINAC axes.

* * * * *